United States Patent [19]

Evans et al.

[11] 4,130,250

[45] Dec. 19, 1978

[54] REELS FOR MEDICAL TRACTION APPLICATIONS

[75] Inventors: Mervyn Evans, Oxford; John D. Harris, Abingdon, both of England

[73] Assignee: The Secretary of State for Social Services in Her Britannic Majesty's Government of the United Kingdom of Great Britain and Northern Ireland, London, England

[21] Appl. No.: 834,356

[22] Filed: Sep. 19, 1977

[30] Foreign Application Priority Data

Sep. 24, 1976 [GB] United Kingdom ............... 39884/76

[51] Int. Cl.² ........................ B65H 17/02; A61H 1/02
[52] U.S. Cl. ....................................... 242/68; 128/75; 128/84 B
[58] Field of Search ................ 242/68, 75.43, 67.1 R, 242/54.1; 128/75, 84 R, 84 B, 84 C; 192/41 S; 188/82.6

[56] References Cited

U.S. PATENT DOCUMENTS

| 1,615,804 | 1/1927 | Starkey | 192/41 S |
| 1,674,009 | 6/1928 | Holmes | 192/41 S |
| 2,488,058 | 11/1949 | Fleishman | 128/84 B |
| 3,559,907 | 2/1971 | Somervell | 242/54.1 |
| 3,683,900 | 8/1972 | Alessi | 128/84 C |
| 3,878,842 | 4/1975 | Goldberg | 128/84 C |

*Primary Examiner*—Edward J. McCarthy
*Attorney, Agent, or Firm*—Pollock, Vande Sande and Priddy

[57] ABSTRACT

A reel for use upon a cylindrical support on plaster jacket bedframes incorporates a ratchetless anti-reverse mechanism which is readily disengageable and which permits continuous adjustment of the position of the reel upon the bedframe. The anti-reverse mechanism comprises a close wound helical spring which has a free diameter less than the diameter of the cylindrical support. The spring is mounted on the cylindrical support and attached by one of its ends to a spool rotatably mounted on the cylindrical support.

7 Claims, 3 Drawing Figures

REELS FOR MEDICAL TRACTION APPLICATIONS

This invention relates to a reel for medical usage where it is required to apply traction, restraint, or support to a patient by tightening a cord or tape. The reel is particulary, but not exclusively, intended for use in conjunction with a bed-like framework from which traction may be applied to a patient by means of reels mounted upon the framework. Such frameworks are commonly used when applying a plaster cast to a patient and consequently will be referred to hereinafter as plaster jacket bedframes.

Prior plaster jacket bedframes have been difficult to use effectively because the reels were mounted on the framework such that only preselected sites were available. Because the reel position was not continuously adjustable it was frequently impossible to apply the traction exactly where required. Also prior reels used on such plaster jacket bedframes incorporated ratchet anti-reverse mechanisms which were difficult to disengage, to enable the patient to be released, without first applying additional traction to the patient.

The present invention provides a reel primarily, but not exclusively, for use in conjunction with a plaster jacket bedframe which is easily and continuously adjustable in position upon the bedframe and which incorporates a ratchetless anti-reverse mechanism which is easy to disengage without the application of further traction to the patient.

The invention is a reel for applying traction, restraint, or support to a patient, comprising a spool and a close wound helical spring which is coaxially attached to the spool by one of its ends; whereby in use the spool and the spring are set upon a cylindrical support having a slightly greater diameter than the free internal diameter of the spring so that the spring encircles and grips the support, rotation of the spool in one direction expanding the spring to free its grip and contra-rotation of the spool being resisted by the grip of the spring. The reel may be released to permit such contra-rotation by turning the other end of the spring in the direction of said contra-rotation so expanding the spring and freeing its grip.

Preferably the said other end of the spring is operatively connected to an end cap of the reel; whereby in use the end cap is also mounted on the cylindrical support, movement of the end cap in the direction of said contra-rotation expanding the spring to free its grip and permit said contra-rotation of the spool.

Traction is applied to the patient by attaching a traction tape or cord to the reel and by turning the spool by hand in the direction such that the spring grip is released. Such traction will automatically be maintained by the spring grip when the turning force is removed, but may be released by turning the end cap upon the support. Thus the traction may be removed easily without applying further force to the patient. By turning the end cap relative to the spool in the direction such that the diameter of the spring is enlarged, the reel may be freely moved along the cylindrical support to any position required.

Preferably the spring is made of substantially flat strip to ensure maximum area of contact with the surface of the cylindrical support. Preferably such a spring should have at least 6 turns, a number of 8¼ being presently adopted.

A tape or cord is wound upon the spool and tightened by the reel to apply traction to the patient and this is required to be removable from both the spool and the patient after traction. Where a plaster cast has been applied to the patient it may be necessary to remove the tape by drawing it through the body of the plaster. Consequently tapes having buckles or other fastenings cannot be withdrawn intact. Means may therefore be provided whereby a plain end of tape or cord may be secured to the spool by overlying turns. Preferably this means comprises a rod juxtaposed with the spool so that a plain end may be wrapped around the rod to trap it.

The invention will now be described, by way of example only, with reference to the accompanying drawings, in which.

Figure 1:
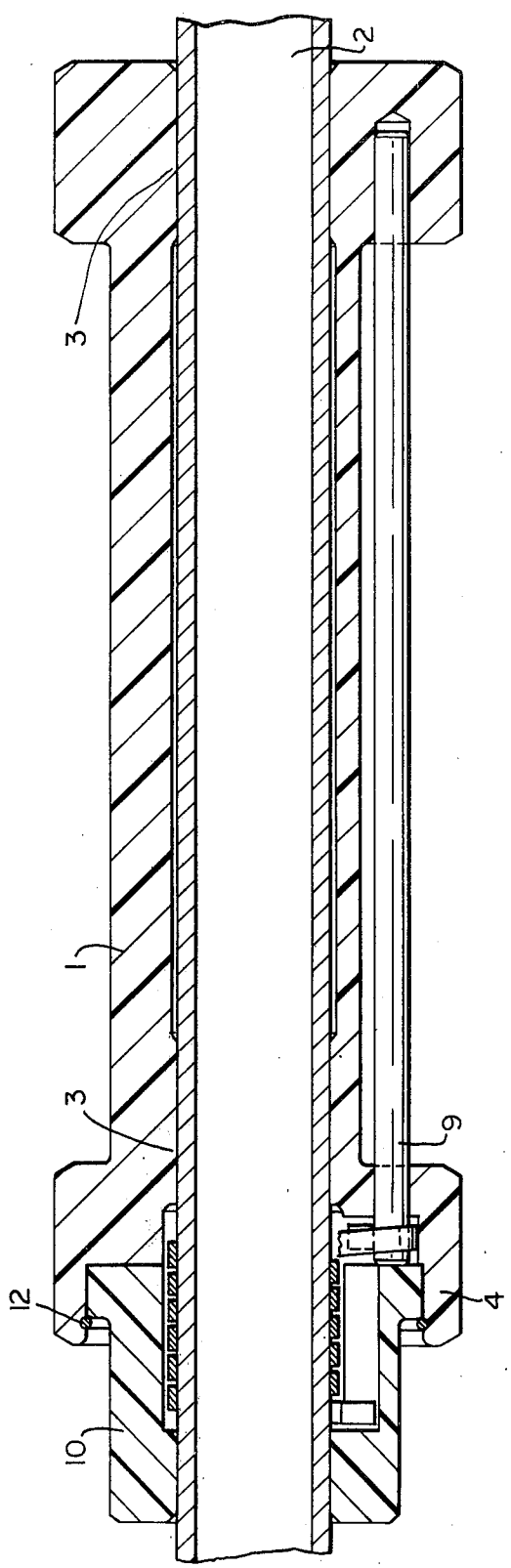
FIG. 1 is a longitudinal sectional view of the reel.
Figure 2:
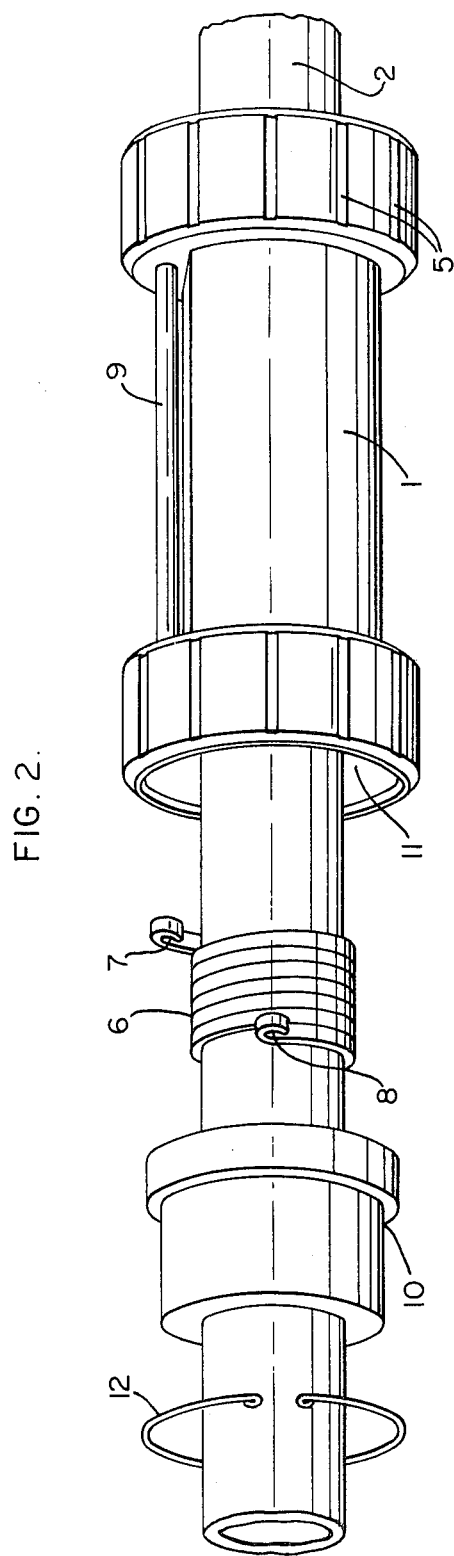
FIG. 2 is an exploded diagram of the reel illustrated in FIG. 1.

The construction of the reel can be easily seen by reference to FIGS. 1 and 2 in which common reference numerals are used. A shallow elongate spool 1 of plastics material is shown, suitable for receiving several layers of a wide traction tape (not shown). The spool 1 is rotatably mounted upon a cylindrical support 2 of stainless steel tube by means of a throughbore in the spool 1 and bears upon the support 2 at bearing portions 3 that are situated one at each end of the throughbore. Intermediate the bearing portions 3, the throughbore is of sufficient size to adequately clear the cylindrical support 2 so that minor irregularities therein, such as slight bends, do not cause the spool 1 to sieze. At its ends, the spool 1 is provided with diametrically enlarged portions 4 which serve as flanges to prevent the lateral displacement of a traction tape wound thereon and provide good handling surfaces by which the spool 1 may be turned to wind the traction tape thereon. The enlarged portions 4 may be provided with grooves 5 for a better handgrip or to enable a "C" spanner to be applied in the unlikely event of this being necessary.

Adjacent one end of the spool 1, and coaxially mounted with this upon the cylindrical support 2, is a close wound helical spring 6 having looped end portions 7 and 8. The free internal diameter of the spring 6 is less than the external diameter of the cylindrical support 2 so that the spring 6 needs to be diametrically enlarged to fit thereon. The tension in the spring 6 when diametrically enlarged so that it fits upon the cylindrical support 2 enables the spring 6 to grip the cylindrical support. The tensile force that may be applied to the end 7 of the spring 6 before this turns upon the cylindrical 2 support may be determined by capstan theory and is proportional to $e^{\mu\theta}$, where $\mu$ is the coefficient of friction and $\theta$ is the total angular rotation of the spiral spring 6 (ie 360° × the number of turns). It has been found by experiment that a minimum of six spring turns are required to operate satisfactorily in a manner to be described later but for the present application a spring of 8¼ turns is used and this is of flattened form as shown to increase the frictional engagement between the spring 6 and the cylindrical support 2. The free internal diameter of this spring is nominally 26mm while the external diameter of the cylindrical support 2 is nominally 27 mm so that an angular movement of 100° of one end of the spring with respect to the other is required to provide the necessary diametrical enlargement for the spring 6 to fit upon the cylindrical support 2.

The looped end 7 of the spring 6 is a tight fit upon a rod 9 which secures it to the end of the spool 1, the rod also being juxtaposed with the spool body so that a plain end of a traction tape may be looped around it to be secured by overlying turns wound upon the spool 1. At its other end 8 the spring 6 is operatively connected to an end cap 10 by means of a recess therein. This operative connection may also be a pinned joint but this is not essential to the operation of the capstan device and the more simple joint shown results in easier assembly of the device. The end cap 10 locates within a cylindrical recess 11 in the end of the spool 1 and is secured therein by means of a circlip 12 in a position such that the spring 6 is completely covered by the end cap 10 and the spool 1.

Operation of the capstan device is as follows. Firstly one end of the traction tape is secured to the patient and the other end is passed around the rod 9 so that it lies beneath the first turn of tape to be wound upon the spool 1. Then the spool 1 is turned by hand in a direction such that it pushes the end 7 of the spring 6 against the direction of lay of the spring 6 so enlarging its diameter sufficiently to release on the cylindrical support 2. When the turning force on the spool 1 is removed the spring 6 relaxes to grip the cylindrical support 2 once more and prevent contra-rotation of the spool 1. Thus the force to be applied to the patient may be gradually increased at will to any required level and will automatically be maintained. When release of the force is required the end cap 10 is turned against the lay of the spring 6 and in the direction of the required contra-rotation to release the grip of the spring 6. Thus the force may be gradually and swiftly released at will without the imposition of additional forces on the patient.

Figure 3:
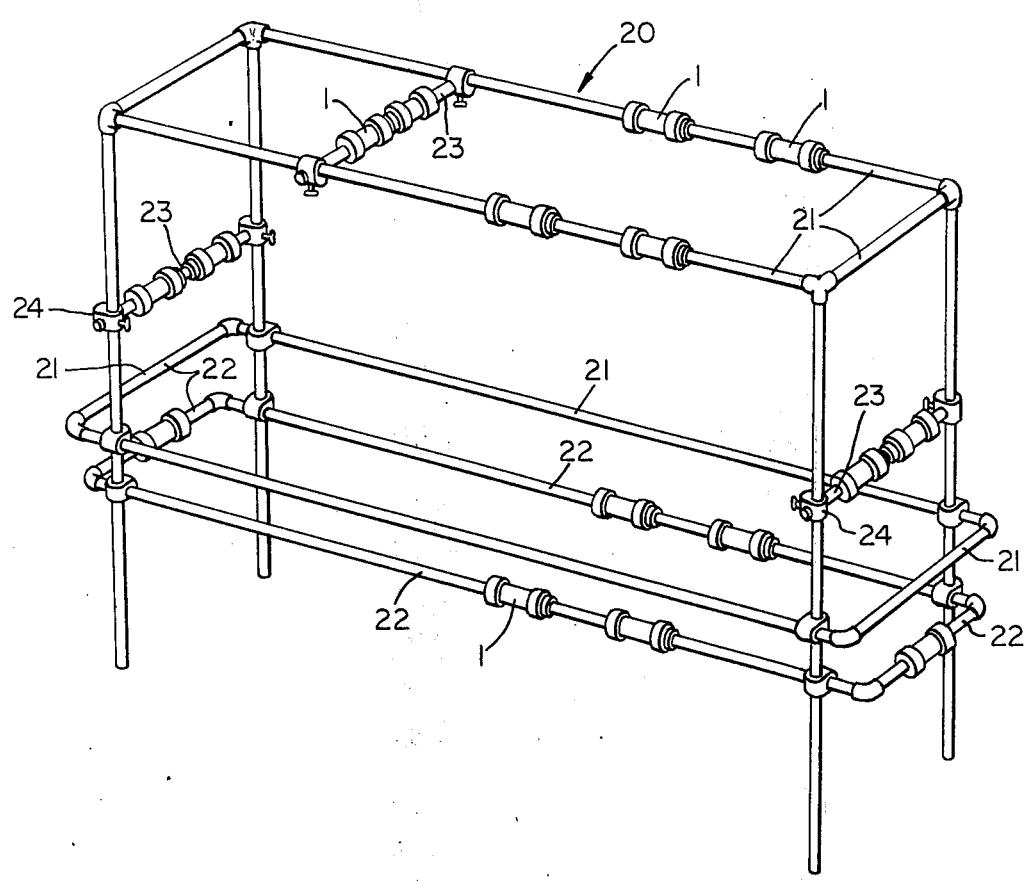
FIG. 3 is an isometric projection showing a plaster jacket bedframe incorporating the reels illustrated in FIGS. 1 and 2.

FIG. 3 is a diagram illustrating the principal use of the reel, in conjunction with a plaster jacket bedframe generally indexed 20. The bedframe 20 comprises an array of rigid metal tubes connected together in scaffolding like fashion to form a main frame 21 and a sub frame 22. Cross tubes 23 link parallel tubes of the main frame 21 and are fastened thereto by releasable connections 24 so that the cross tubes 23 may be slid along their corresponding parallel tubes of the main frame. Reels 1 of the type described with reference to FIGS. 1 and 2 are positioned anywhere where they are required on the main frame 21, the sub frame 22 and the cross tubes 23. They can be slid along any one of these tubular supports to exactly the position required. Thus a patient may be supported within the bedframe 20 by tapes carried by the reels on the sub frame 22 and traction may be applied by any of the reels mounted on the main frame 21 or cross tubes 23.

The invention has been described by way of example only, to enable the reader to fully understand the principles of the invention and the construction of the presently preferred embodiment but this description is not intended to limit the scope of the invention as defined by the attached claims. Many variations of the embodiment described, obvious to those of ordinary skill in the art, are within the scope of the invention. For instance the endcap 10 is not an essential feature as forces may be applied directly to the end 8 of the spring 6, and the materials used in construction are used for convenience only and are not essential. The spool 1 shown is suitable for receiving wide traction tapes (15.5cm) but narrower tapes or cords may require different spool shapes. Additionally the invention is not restricted to use in conjunction with plaster jacket bedframes but may be used for many medical applications where traction, support, or restraint is required.

We claim:

1. A reel for applying traction, restraint, or support to a patient, comprising a spool, a close wound helical spring which is coaxially attached to the spool by one of its ends, and an end cap operatively connected to the other end of said spring; whereby in use the spool, spring, and end cap are mounted on a cylindrical support having a slightly greater diameter than the free internal diameter of the spring so that the spring encircles and grips the support, rotation of the spool in one direction expanding the spring to free its grip and contra-rotation of the spool being resisted by the grip of the spring while rotation of the end cap in the contra-rotation direction expands the spring to release its grip and permit said contra-rotation of said spool.

2. A reel as claimed in claim 1 in which the close wound helical spring is made of substantially flat strip to ensure maximum area of contact with the cylindrical support.

3. A reel as claimed in claim 1 in which the close wound helical spring has at least six turns.

4. A reel as claimed in claim 3 in which the close wound helical spring has eight and one quarter turns.

5. A reel as claimed in claim 1 having securing means whereby a plain end of tape may be secured to the spool by overlying turns.

6. A reel as claimed in claim 5 in which the securing means comprises a rod fixed to the spool in a juxtaposed position.

7. A medical appliance comprising at least one cylindrical support member and at least one reel as claimed in claim 1.

* * * * *